(12) United States Patent
Hassler

(10) Patent No.: US 6,478,758 B1
(45) Date of Patent: Nov. 12, 2002

(54) SPLINT SYSTEM

(76) Inventor: Andreas Hassler, Ranhartstetten 10, D-83101 Rohrdorf (DE)

( * ) Notice: Subject to any disclaimer, the term of this patent is extended or adjusted under 35 U.S.C. 154(b) by 0 days.

(21) Appl. No.: 09/626,051

(22) Filed: Jul. 26, 2000

(30) Foreign Application Priority Data

Jul. 28, 1999 (DE) .......................................... 199 35 058

(51) Int. Cl.⁷ ................................................ A61F 5/00
(52) U.S. Cl. ............................................ 602/5; 602/16
(58) Field of Search .......................... 473/450; 128/846, 128/869, 877, 878, 879, 882; 602/4, 5, 20, 21

(56) References Cited

U.S. PATENT DOCUMENTS

| | | | |
|---|---|---|---|
| 612,087 A | * | 10/1898 | Boyd |
| 3,028,858 A | * | 4/1962 | Cutler .......................... 602/20 |
| 4,657,000 A | | 4/1987 | Hepburn |
| 5,328,446 A | | 7/1994 | Bunnell et al. |
| 5,403,002 A | * | 4/1995 | Brunty ...................... 273/55 R |
| 5,741,220 A | | 4/1998 | Brink |
| 5,865,695 A | * | 2/1999 | Mahala ......................... 602/20 |

FOREIGN PATENT DOCUMENTS

| | | |
|---|---|---|
| DE | 79 03 618 U1 | 2/1979 |
| EP | 0 413 523 A2 | 2/1991 |
| WO | WO 93/02644 | 2/1993 |
| WO | WO 95/23568 | 9/1995 |

* cited by examiner

Primary Examiner—Michael A. Brown
(74) Attorney, Agent, or Firm—McGlew and Tuttle, P.C.

(57) ABSTRACT

A splint system (10) is provided with a hinged splint device (11) with hinge levers (16, 17), which are connected via a hinge device (18), and with securing elements (12, 13, 14, 15) arranged on the hinged splint device (11) for fixing the hinged splint device (11) to body parts. The securing elements (12, 13, 14, 15) form units, which can be handled independently of the hinged splint device (11) and can be fixed at least in the longitudinal direction of the hinge levers (16, 17) at chosen securing sites within a securing region (59) of the hinge levers (16, 17) via a connecting device (31).

17 Claims, 3 Drawing Sheets

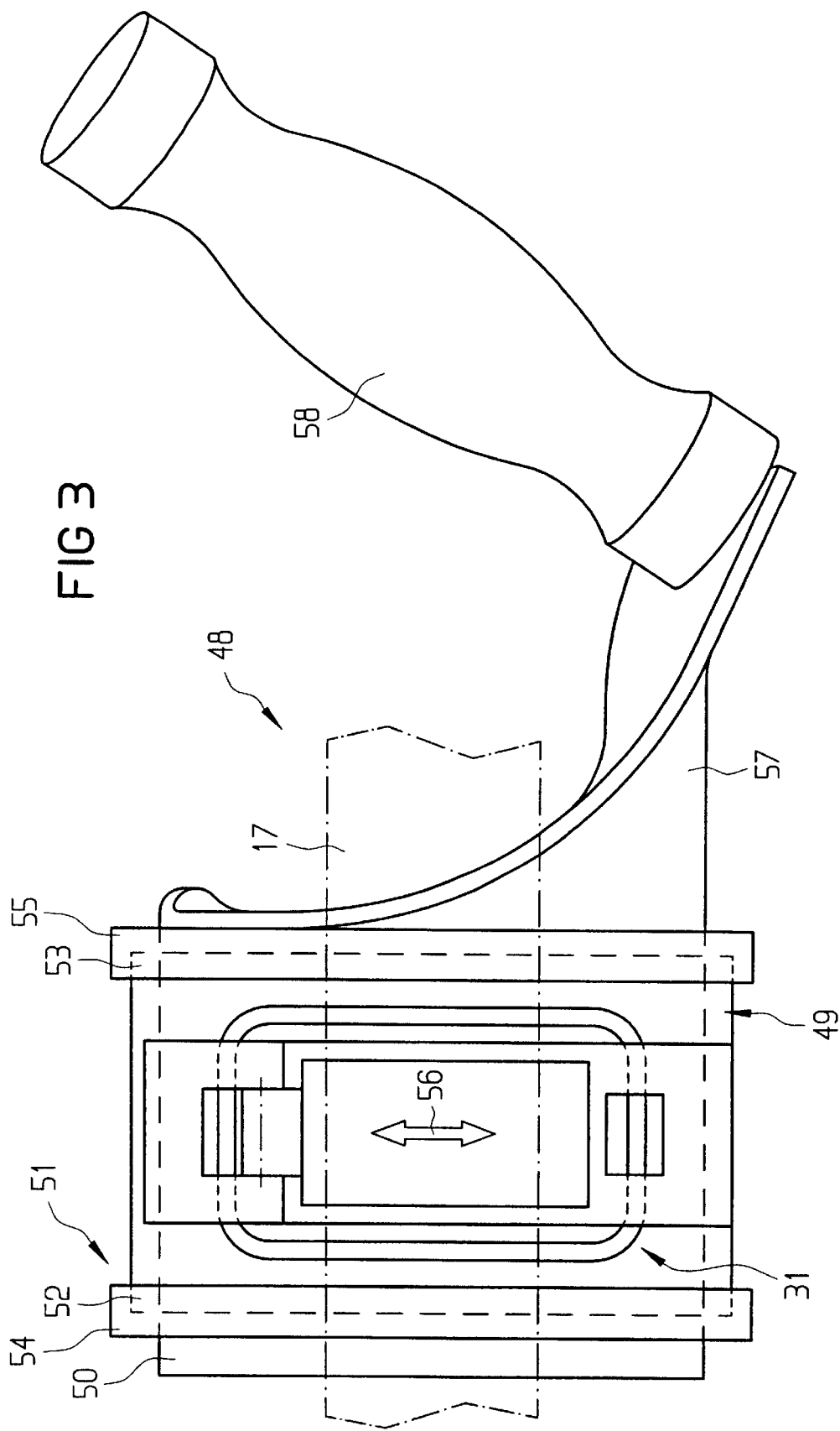

SPLINT SYSTEM

FIELD OF THE INVENTION

The present invention relates to a splint system with a hinged splint device with hinge levers, which are connected to one another via a hinge device, and with securing elements arranged on the hinged splint device for fixing the hinged splint device to body parts.

BACKGROUND OF THE INVENTION

Splint systems of the above mentioned type are usually used for carrying out a so-called joint fixing, in which body parts of extremities which are connected to one another via a body joint so as to be movable relative to one another are fixed relative to one another in a given relative position by means of the hinge levers, in order to steady the joint. In addition, depending on the design of the hinge device, splint systems of this type are also used for active therapy, in which a movement range adjustable by means of the hinge device for carrying out a bending or straightening movement is allowed, for example, or a resistance force is superimposed upon a bending or straightening movement, which allows for the use of splint systems of this type as socalled "Quengel splints".

Irrespective of the particular type of use of the splint systems in detail, it has proved important for the success of therapeutic treatment on the one hand for a good fixing of the hinge levers to the body parts adjacent the body joint to be provided, and on the other hand for the hinged splint device to be fixed to the body parts in question in such a manner that the axis of rotation of the hinge device is arranged as far as possible coaxial to the axis of rotation of the body joint.

As a result of these extensive requirements which are made of the fit of a hinged splint device, a correspondingly high adaptation outlay results when fitting the hinged splint device to the adjacent body parts of the body joint in question. This adaptation outlay is even repeated if—as is often the case in joint therapy—it is only necessary to wear the hinged splint device periodically, so that with each fitting procedure it is necessary to carry out the adaptation of the hinged splint device anew in order to obtain the desired fit.

Furthermore, a considerable restriction in wearing comfort often results from the non-variable arrangement of the securing elements on the hinge levers of the hinged splint device. Thus, it may occur as a result of the fixed arrangement of the securing elements relative to the hinge levers, that a fixing of the hinge levers is required in regions of the body parts which are particularly sensitive to pain, for example in regions with scar tissue.

SUMMARY AND OBJECTS OF THE INVENTION

It is the object of the present invention to propose a splint system which in a particularly simple manner allows for an adaptation of the relative arrangement of the securing elements relative to the hinge levers and which in addition considerably reduces the adaptation outlay when fitting the hinged splint device.

According to the invention, a splint system is provided with a hinged splint device with hinge levers, which are connected via a hinge device, and with securing elements arranged on the hinged splint device for fixing the hinged splint device to body parts. The securing elements form units, which can be handled independently of the hinged splint device and can be fixed at least in the longitudinal direction of the hinge levers at chosen securing sites within a securing region of the hinge levers with a connecting device.

In the splint system according to the invention, the securing elements form units, which can be handled independently of the hinged splint device and can be fixed at least in the longitudinal direction of the hinge levers at chosen securing sites within a securing region of the hinge levers by means of a connecting device.

As a result of the separate handling of the securing elements independently of the hinged splint device, it is possible, in complete contrast to the convention type and manner, to fit a hinged splint device to an extremity, to fix securing elements at the selected sites of the body parts in a first step, and only then, in a second step, to connect the hinge levers of the hinged splint device to the securing elements in such a manner that an optimal fit of the hinged splint device results—particularly in respect of a coaxial arrangement of the swivel axis of the hinged splint device and the swivel axis of the body joint.

For the periodic removal of the hinged splint device from the extremity, the securing elements can remain on the hinge levers of the hinged splint device, so that during repeated fitting of the splint system the hinged splint device can also be fitted in conjunction with the securing elements.

The fitting of the securing elements independently of the hinged splint device results in the particular advantage that the fixing positions of the securing elements on the respective body parts are selectable, so that in a special manner it is possible to take account of individual peculiarities of the body parts of the person in question, such as skin injuries, for example.

Also with a view towards frequent use or reuse of the splint system on different persons, the design of the splint system according to the invention has proved advantageous, since the securing elements can be easily replaced as those elements which come into direct physical contact with the patient, whilst the hinged splint device can be used as often as desired by different people.

In an advantageous embodiment, the connecting device of the securing elements is constructed in such a manner that, in a first connecting position, a connection is produced between the securing elements and the hinge lever acting transversely to the longitudinal direction of a hinge lever and, in a second connecting position, a connection is produced acting both transversely to the longitudinal direction and in the longitudinal direction. In this manner, the installation of the hinged splint device on the securing elements already fixed to the respective body parts is considerably facilitated, since in the first connecting position a securing of the hinged splint device to the securing elements is achieved. However, in this first connecting position a relative movement in the longitudinal direction of the hinge levers is also possible, thereby considerably facilitating a precise adjustment with the aim of coaxially aligning the swivel axes of the hinge device and the body joint relative to one another. It is then only possible to carry out a final fixing of the hinge levers of the hinged splint device to the securing elements by means of the second connecting position.

If the connecting device is constructed as a clamping device, with a clamping draw line guided over a clamping plate, which clamping line can be transferred by means of a switching lever lockable on the clamping plate from a relatively released state in the first connecting position into a relatively tensioned state in the second connecting position, it is possible during the fixing of the securing elements relative to the hinge levers to adjust a relative rotation of the securing elements relative to the hinge levers about a surface normal of the clamping plate. In this manner, the adaptation possibilities to the individual peculiarities of the respective body part are further increased.

A further increase in the adaptation possibilities is possible if the clamping plate is connected via a swivel hinge to a support collar for the enclosing accommodation of a body part, and the swivel hinge comprises—a swivel axis which, is arranged transversely to the longitudinal axis of the hinge lever.

A realization of the swivel hinge on the securing element which is particularly cost-effective in respect of manufacturing costs is possible if the swivel hinge is constructed as a film hinge between the clamping plate and the support collar. In this manner, the securing elements are manufactured on the basis of a moulded plastics material part, for example manufactured in a two-part injection mould, comprising the clamping plate and the support collar.

In order to fix the securing element to a body part, according to an advantageous embodiment a securing strap enclosing the support collar is provided, which comprises a positioning slot for the positioning arrangement of the securing strap on the film hinge of the support collar. In this design, the film hinge is therefore simultaneously used for positioning or fixing the securing strap on the securing element.

It has proved particularly advantageous with a view towards universal use of the splint system if the hinge levers are replaceably connected to the hinge device of the hinged splint system. In this manner, it is possible, on the one hand, to select the hinge levers in their dimensioning according to the body parts to which they are to be fixed by means of the securing elements. On the other hand, depending on the indication, different types of hinge devices can be combined with the hinge levers, for example, a hinge device with a torsion spring device in order to use the splint system as a "Quengel splint".

The splint system forms a sort of component or module system with the hinge device, the hinge levers and the securing elements as individual modules which can be combined with one another. Furthermore, it is also possible to supplement the splint system with further modules, which need not have a securing function, but can also have a purely therapeutic function, such as optionally actively operable training devices or even simple holding devices, such as fixed or movable stops or handles. On account of the resulting wide range of design variations, it is possible for example to specially adapt the splint system for use as a "Quengel splint" on the ankle, for example for the therapeutic treatment of a straightening deficit in the ankle following an Achilles tendon injury.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 3 is a detailed view of a securing element in a design as a rotary securing element.

DESCRIPTION OF THE PREFERRED EMBODIMENT

Figure 1:
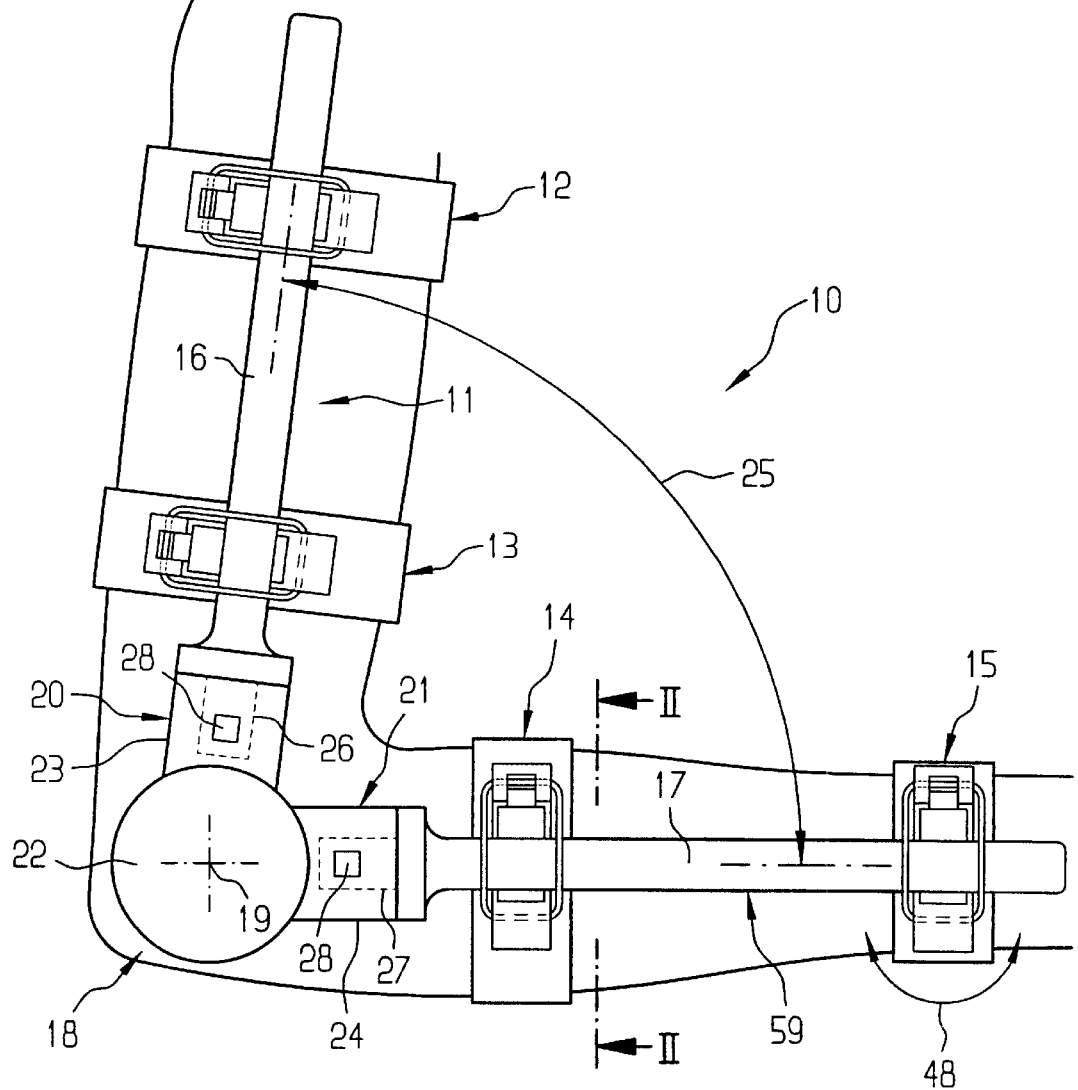
FIG. 1 is a front view showing a splint system fitted to the right arm of a patient with a hinged splint device and securing elements arranged thereon.

Referring to the drawings in particular, FIG. 1 shows a splint system 10 with a is hinged splint device 11 and securing elements 12, 13, 14 and 15. The hinged splint device 11 comprises two hinge levers 16, 17, which are articulatedly connected to one another via a hinge device 18. The hinge device 18 comprises two swivel hinge elements 20, 21 arranged on a common swivel hinge axle 19, each with a hinge disk 22, on which a connecting extension 23, 24 is constructed for connection with a hinge lever 16, 17. Furthermore, the hinge device 18 is provided with swivel locking means, not shown here in detail, so that a desired bending angle 25 can be adjusted on the hinged splint device 11.

At their connecting ends, the hinge levers 16, 17 comprise connecting tongues 26, 27, which are connected to the respective hinge elements 20, 21 of the hinge device 18 by introduction into the connecting extensions 23, 24 and locking by means of a releasable locking device 28.

As shown in FIG. 1, in the indication selected by way of example in FIG. 1, the hinge lever 16 and the hinge lever 17 are fixed to the upper arm and lower arm respectively in a securing region 59 by means of the two securing elements 12, 13 and 14, 15. In the illustrated example, all securing elements 12, 13, 14 and 15 can be of identical design, so that for the detailed description of the securing elements reference will be made in the following by way of example to the securing element 14, which is arranged on the lower arm in the region of the elbow joint.

Figure 2:
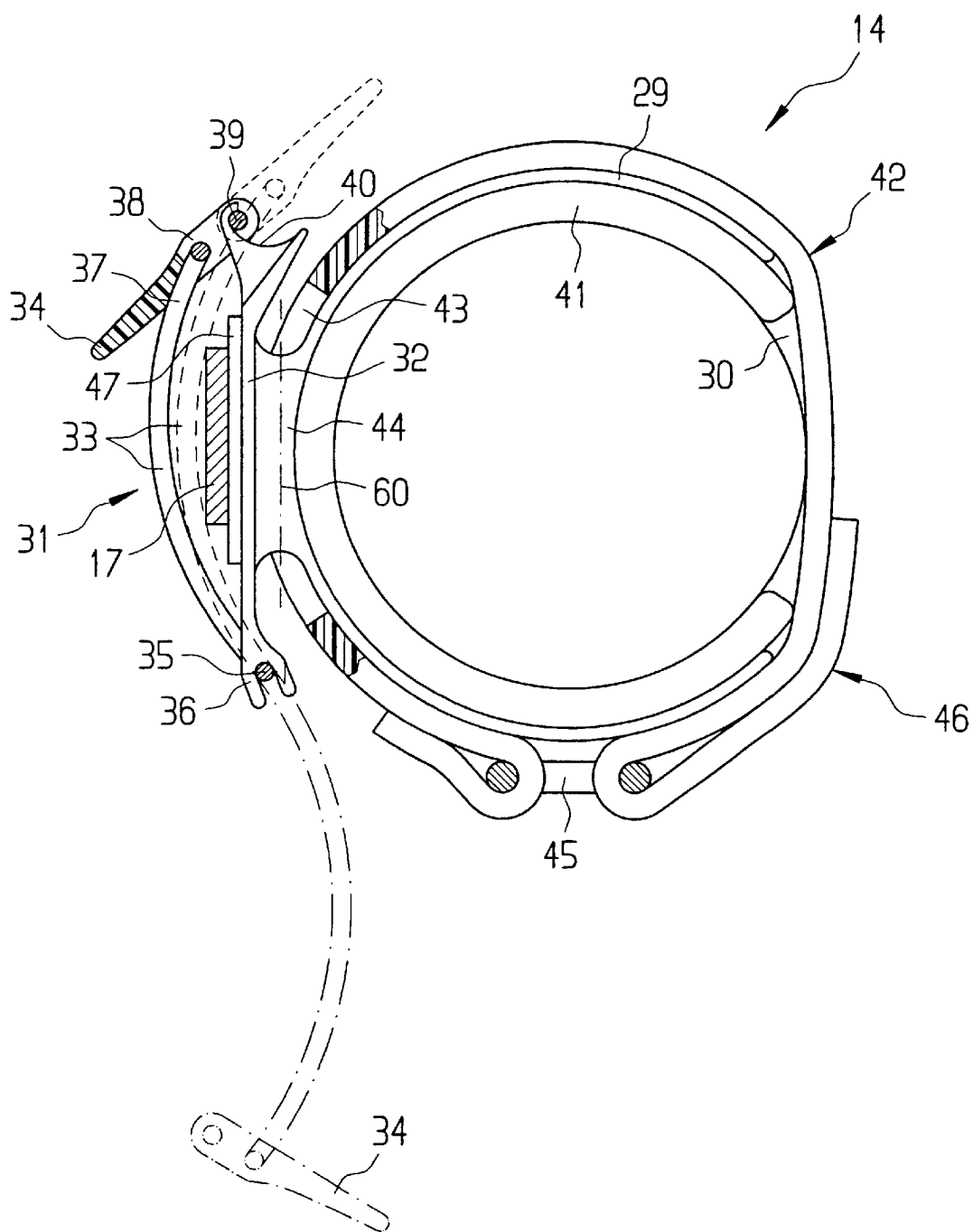
FIG. 2 is a side view of a securing element illustrated in FIG. 1 taken along the line of section II–II in FIG. 1.

As is clear from FIG. 1 and in particular from the detailed view of the securing element 14 according to FIG. 2, the securing element 14 comprises a support collar 29, which in this case is approximately C-shaped and opposite a recess 30 for laterally pushing the securing element 14 onto the lower arm shown in section in FIG. 2 comprises a connecting device 31 for connection to the hinge lever 17. The connecting device 31 comprises a clamping plate 32, over which a clamping draw line 33 extends, which can be transferred by means of a switching lever 34 from a released into a tensioned state. To this end, the clamping draw line 33, which in the present case is constructed as a closed cable loop, is accommodated with an end region 35 at one end of the clamping plate 32 in a clamping recess 36. An opposite end region 37 of the clamping draw line 33 is arranged in a clamping draw line recess 38 of the switching lever 34 at a distance a from a pivot axis 39 of the switching lever 34. In order to construct the pivot axis 39, the switching lever 34 is pivotably arranged in a lever recess 40 constructed on the clamping plate 32.

As also visible from FIG. 2, the connecting device 31 allows for two connecting positions, namely a first prefixing position, illustrated in the present case by continuous lines, and a second fixing position, shown in the illustrated embodiment by broken lines.

These different connecting positions will be explained in further detail in the following in the course of a further description of the fitting procedure for fitting the splint system 10 to the extremity shown in FIG. 1.

In order to fit the splint system 10, a fixing of the securing elements 12, 13, 14 and 15 to the selected sites of the upper arm and lower arm is firstly effected. Securing sites may be any selected site at any location (numerous arbitrary selectable positions) along the securing region 59 of each of the hinge levers 16 and 17. To this end, the securing element 14, for example, is pushed with its support collar 29 laterally onto the selected site of the lower arm in the region of the elbow joint. As a result of the geometrically elastic construction of the support collar 29, an initial expansion is followed by an at least partially intimate fit of the support collar, a pressure cushion 41 being arranged on the inside of the support collar 29 between the support collar 29 and the lower arm. In order to fix the securing element 14 in this position, a securing strap 42 is arranged on the support collar 29, which for positioning on the support collar 29 comprises a slot 43, through which a film hinge 44 projects, which connects the support collar 29 to the clamping plate 32 of the connecting device 31. The slot 43 has a width of sufficient size, so that the securing strap 42 can be fitted over the connecting device 31 and, as shown in FIG. 2, brought into abutment with the surface of the support collar 29. With one end region, the securing strap 42 is fixed to a connecting eyelet 45, with its other end region, which is constructed as a Velcro fastening 46, the securing strap is guided through the connecting eyelet 45 and secured to the connecting eyelet 45.

Following the securing of the securing elements 12, 13, 14 and 15 to the extremity as described above, a preliminary fixing of the hinged splint device 11 to the securing elements 12, 13, 14 and 15 is effected in such a manner that in an open state of the connecting device 31, in which the switching levers 34 are disengaged from the lever recess 40 and as shown in FIG. 2 by the dot-dash line, hang down from the clamping plate 32 held by the clamping draw line recess 36, the hinged splint device 11 is positioned with the hinge levers 16, 17 against a friction insert 47 of the clamping plate 32 and then the connecting devices 31 are transferred into their preliminary so fixing position illustrated in continuous lines in FIG. 2 by producing the locking connection between the switching lever 34 and 14 the lever recess 40. In this position, the hinged splint device 11 is held in a manner secured against loss at the securing elements 12, 13, 14 and 15, although relative movements are possible, more particularly in the direction of the longitudinal axes of the hinge levers 16, 17. When the connecting devices 31 are disposed in their preliminary fixing position, precise positioning of the hinged splint device 11 to the extremity can be effected in such a manner that the swivel hinge axis 19 of the hinge device 18 is aligned substantially coaxial to the elbow joint axis. During this fuze adjustment, it is possible, as a result of the design of the connecting devices 31 as clamping devices with a flat clamping plate in this case, to arrange the hinge levers 16, 17 rotated or pivoted in the plane of the clamping plate 32, as indicated by the double arrow 48 in FIG. 1. In addition, it is possible to take into account additional inclined positions by a pivoting of the clamping plate 32 about a swivel axis 60 of the hinge joint 44.

Once the exact desired relative positioning, between the securing elements 12, 13, 14, and 15, is obtained, the connecting device 31 can be transferred by switching the switching lever 34 into the fixing position illustrated in FIG. 2 by broken lines. In this position, the hinge levers 16, 17 are secured in their position relative to the securing elements 12, 13, 14, 15 as a result of the clamping force transmitted to the hinge levers 16, 17 by the clamping draw lines 33.

In contrast to the explanation of the splint system 11 given above with reference in particular to FIG. 1, which in FIG. 1 is provided with four identically constructed securing elements, it is also possible to effect an adaptation of the shape and function of the securing elements to specific indications according to the embodiment of a securing element 48 illustrated in FIG. 3.

In the securing element 48 illustrated in FIG. 3, the connection between a clamping plate 49 and a support collar 50 is not effected by means of a film hinge 44, as shown in FIG. 2 by way of example of the securing element 14, but via a sliding hinge connection 51, in which the clamping plate 49 is constructed in the manner of a ring segment and is displaceably guided on the support collar 50 in the manner of a slipper with guide edges 52, 53 in groove guides 54, 55 in the direction of the movement arrow 56. At the same time, the support collar 50 is provided on a longitudinal extension 57 with a handle 58, which can be grasped by the hand. In a fixing position of the connecting device 31 illustrated in FIG. 3, the clamping plate 49 is therefore fixed relative to the hinge lever 17, so that the wrist, not shown in further detail here, can carry out a rotational movement relative to the hinge lever 17 together with the support collar 50 by grasping the handle 58 with the hand.

The securing element 48 illustrated in FIG. 3 can be replaced, for example, by the securing element 15 illustrated in FIG. 1, in order to realize a splint system which with a given indication allows for a movement induction in the tendon apparatus of the elbow joint by a possible rotation of the wrist at the hinged splint device 11.

While a specific embodiment of the invention has been shown and described in detail to illustrate the application of the principles of the invention, it will be understood that the invention may be embodied otherwise without departing from such principles.

What is claimed is:

1. A splint system with a hinged splint device, the splint system, comprising:
   a hinge device;
   hinge levers connected via said hinge device to provide a lower hinge lever with a securing region and an upper hinge lever with a securing region;
   a plurality of securing elements arranged on the hinged splint device for fixing the hinged splint device to body parts, said securing elements forming units, each unit being handled independently of the hinged splint device and having a connecting device fixing the hinged splint device to body parts at least in the longitudinal direction of said hinge levers at chosen securing sites at any location along said securing region of said upper hinge lever and at chosen securing sites at any location along said securing region of said lower hinge lever.

2. A splint system according to claim 1, wherein said connecting device, in a first connecting position, produces a connection between the securing elements and one of said hinge levers, acting trasversely to the longitudinal direction of said one of said hinge levers and, in a second connecting position, producing a connection acting both transversely to the longitudinal direction and in the longitudinal direction.

3. A splint system according to claim 1, wherein said connecting device includes a clamping device, with a clamping draw line which is guided over a clamping plate and with a switching lever lockable on said clamping plate for transitioning from a relatively released state in said first connecting position into a relatively tensioned state in said second connecting position.

4. A splint system according to claim 3, wherein said clamping plate is connected via a swivel hinge with a support collar for an enclosing accommodation of a body part, and said swivel hinge comprises a swivel axis, which is arranged transversely to a longitudinal axis of said hinge lever.

5. A splint system according to claim 4, wherein said swivel hinge is constructed as a film hinge between said clamping plate and said support collar.

6. A splint system according to claim 1, wherein said securing elements each include a securing strap enclosing a support collar and comprising a positioning slot for the positioning arrangement of the securing strap on a film hinge between said clamping plate and said support collar.

7. A splint system according to claim 1, wherein said hinge levers include hinge lever to hinge device connectors and are replaceably connected to said hinge device.

8. A splint system with a hinged splint device, the splint system, comprising:
   a hinge device with a first hinge element rotatable relative to a second hinge element;
   a first hinge lever connected to said first hinge element, said first hinge lever having a securing region with securing sites at any location along said securing region of said first hinge lever;
   a second hinge lever connected to said second hinge element said second hinge lever having a securing region with securing sites at any location along said securing region of said second hinge lever;
   a first securing element unit for fixing the hinged splint device to a body part, said first securing element having a connecting device fixing the first securing element to the body part and to the first hinge lever at one of said securing sites within said securing region of said first hinge lever; and
   a second securing element unit for fixing the hinged splint device to a body part, said second securing element having a connecting device fixing the second securing element to the body part and to the second hinge lever at one of said securing sites within said securing region of said second hinge lever.

9. A splint system according to claim 8, wherein each connecting device of the first securing element and the second securing element provides a first connecting position between the securing element and the associated hinge lever acting transversely to a longitudinal direction of said associated hinge lever and provides a second connecting position acting both transversely to the longitudinal direction and in the longitudinal direction of the associated hinge lever.

10. A splint system according to claim 8, wherein each connecting device of said first securing element and said second securing element said connecting device includes a clamping device, with a clamping draw line which is guided over a clamping plate and with a switching lever lockable on said clamping plate for transitioning from a relatively released state in said first connecting position into a relatively tensioned state in said second connecting position.

11. A splint system according to claim 10, wherein said clamping plate is connected via a swivel hinge with a support collar for an enclosing accommodation of a body part, and said swivel hinge comprises a swivel axis, which is arranged transversely to a longitudinal axis of said hinge lever.

12. A splint system according to claim 11 wherein said swivel hinge is constructed as a film hinge between said clamping plate and said support collar.

13. A splint system according to claim 8, wherein each securing element includes a securing strap enclosing said support collar and comprising a positioning slot for the positioning arrangement of the securing strap on a film hinge of the support collar.

14. A splint system according to claim 8, further comprising a first releasable locking device for replaceably connecting said first hinge lever to said hinge device.

15. A splint system with a hinged splint device, the splint system, comprising:
   a hinge device with a first hinge element rotatable relative to a second hinge element;
   a first hinge lever connected to said first hinge element, said first hinge lever having a securing region with a securing region with securing sites at any location along said securing region of said first hinge lever;
   a second hinge lever connected to said second hinge element said second hinge lever having a securing region with securing sites at any location along said securing region of said second hinge lever;
   a first securing element for fixing the hinged splint device to a body part, said first securing element having a connecting device fixing the first securing element to the body part and including a clamping device for clamping the first securing element to the first hinge lever at one of the securing sites along said securing region of said first hinge lever; and
   a second securing element for fixing the hinged splint device to a body part, said second securing element having a connecting device fixing the second securing element to the body part and including a second securing element clamping device for clamping the second securing element to the second hinge lever at one of said securing sites along said securing region of said second hinge lever.

16. A splint system according to claim 15, further comprising:
   a third securing element for fixing the hinged splint device to a body part, said third securing element having a connecting device fixing the second securing element to the body part and including a third securing element clamping device for clamping the third securing element to the first hinge lever at one of said securing sites within said securing region of the third hinge lever; and
   a fourth securing element for fixing the hinged splint device to a body part, said fourth securing element having a connecting device fixing the first securing element to the body part and including a fourth securing element clamping device for clamping the fourth securing element to the second hinge lever at one of said securing sites within said securing region of the fourth hinge lever.

17. A splint system according to claim 16, wherein said second securing element includes a longitudinal extension with a handle to be grasped by the hand of a user of the splint system.

* * * * *